US00PP35986P2

(12) United States Plant Patent
Ruter

(10) Patent No.: US PP35,986 P2
(45) Date of Patent: Jul. 9, 2024

(54) ***ILEX* PLANT NAMED 'RutHol10'**

(50) Latin Name: ***Ilex crenata* x *I. maximowicziana***
Varietal Denomination: RutHol10

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 18/225,819

(22) Filed: Jul. 25, 2023

(51) Int. Cl.
*A01H 5/00* (2018.01)
*A01H 6/00* (2018.01)

(52) U.S. Cl.
USPC ..... Plt./247

(58) Field of Classification Search
USPC ..... Plt./247
CPC ..... A01H 5/12; A01H 5/00; A01H 6/00
See application file for complete search history.

(56) References Cited

PUBLICATIONS

Perishable News.com, Monrovia: Top Ten Distinctive Selections for 2023, retrieved on Nov. 1, 2023 online at https://www.perishablenews.com/floral/monrovia-top-ten-distinctive-selections-for-2023/, 3 pp. (Year: 2022).*

* cited by examiner

*Primary Examiner* — June Hwu
(74) *Attorney, Agent, or Firm* — Thomas | Horstemeyer, LLP

(57) ABSTRACT

A new and distinct cultivar of *Ilex* plant named 'RutHol10' is characterized by a combination of its unique globose habit for plants with this parentage, leaf coloration and upright leaf angle that give 'RutHol10' more of a boxwood (*Buxus*) appearance, and its higher tolerance of spider mites than other *I. crenata* cultivars.

2 Drawing Sheets

Genus and species: Botanical designation: *Ilex crenata* x *I. maximowicziana.*

Variety denomination: The new *Ilex* is of the cultivar denomination 'RutHol10'.

BACKGROUND OF THE INVENTION

The present invention relates to a new and distinct cultivar of *Ilex* holly plant hereinafter referred to by the cultivar name 'RutHol10'.

The new 'RutHol10' variety is a product of a planned breeding program conducted by the inventor in Watkinsville, GA. The objective of the *Ilex* breeding program is to create new plant cultivars with novel forms of growth, good cold hardiness, and resistance to damage from spider mites, insects, and diseases.

The new 'RutHol10' plant is an F2 product of a cross between F1 hybrids of the cross *Ilex crenata* 'Sky Pencil' (unpatented female) x *Ilex maximowicziana* (unpatented, unnamed male parent). The cross was made in Tifton in 2008, and the F1 plants were grown in an isolated block. In spring of 2009 in Tifton, GA, seed was collected from an open pollinated F1 seedling (female) from the original cross. The collected seed was sown in 2009 in Tifton, GA. 'RutHol10', one of the F2 plants grown from the collected seed, was selected for further evaluation in summer of 2018. 'RutHol10' has been evaluated in container production since 2018. 'RutHol10' has been evaluated in field trials at a horticultural farm in Watkinsville, GA since 2019.

Asexual reproduction of the new *Ilex* 'RutHol10' variety was by vegetative terminal cuttings in a controlled environment in Cairo, GA and Watkinsville, GA and has been continued since 2018. Observations of the new variety and resulting progeny have shown that the unique features of this new *Ilex* cultivar 'RutHol10' are stable and have reproduced true to type in successive generations.

SUMMARY OF THE INVENTION

The cultivar 'RutHol10' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Ilex* cultivar named 'RutHol10'. In combination, these traits set 'RutHol10' apart from all other existing varieties of *Ilex* known to the inventor.

1. 'RutHol10' exhibits a unique globose habit for a plant with this parentage.
2. The leaf coloration and upright leaf angle of 'RutHol10' give the plant more of a boxwood (*Buxus*) appearance.
3. 'RutHol10' is more tolerant of spider mites (*Tetranychus*) than *I. crenata* cultivars.

COMPARISON WITH OTHER VARIETIES

Plants of the new *Ilex* 'RutHol10' differ from the most similar *Ilex* cultivars, such as *Ilex crenata* 'Steeds' (unpatented) based on at least some of the following characteristics. The new 'RutHol10' is a male plant, while 'Steeds', in contrast, is a female plant. 'RutHol10' is a faster growing plant than 'Steeds'. In one growing trial, five-year-old (from cutting) 'RutHol10' plants growing in the ground had comparable height, width, and crown density to 'Steeds' plants (3 years in ground, 5 years from propagation). Also, the leaves of the 'RutHol10' plant are larger than the leaves of 'Steeds'. The leaves of the new plant are typically about 3.5 cm long in comparison to leaves of 'Steeds' plants, which are typically 1.2 cm long. Further, the leaves of the 'RutHol10' plants emerge with young growth that is yellow-green (RHS 146A), whereas 'Steeds' is only green (RHS 137A).

All of the F1 male and female plants from the original *I. crenata* x *I. maximowicziana* cross were destroyed. Therefore, a direct comparison cannot be made between 'RutHol10' and the F1 parent plants.

BRIEF DESCRIPTION OF THE FIGURES

The accompanying, colored photographic illustrations show the overall appearance and distinct characteristics of the new cultivar of 'RutHol10' showing the colors as true as possible with the photographic and printing technology utilized. Colors in the photographs may differ slightly from the color values cited in the detailed botanical description. The photographs were taken of three-year-old plants grown outdoors in Watkinsville, Georgia in February of 2022 and are described in the captions below.

The photograph labeled

The photograph labeled

DETAILED BOTANICAL DESCRIPTION

Figure 1:
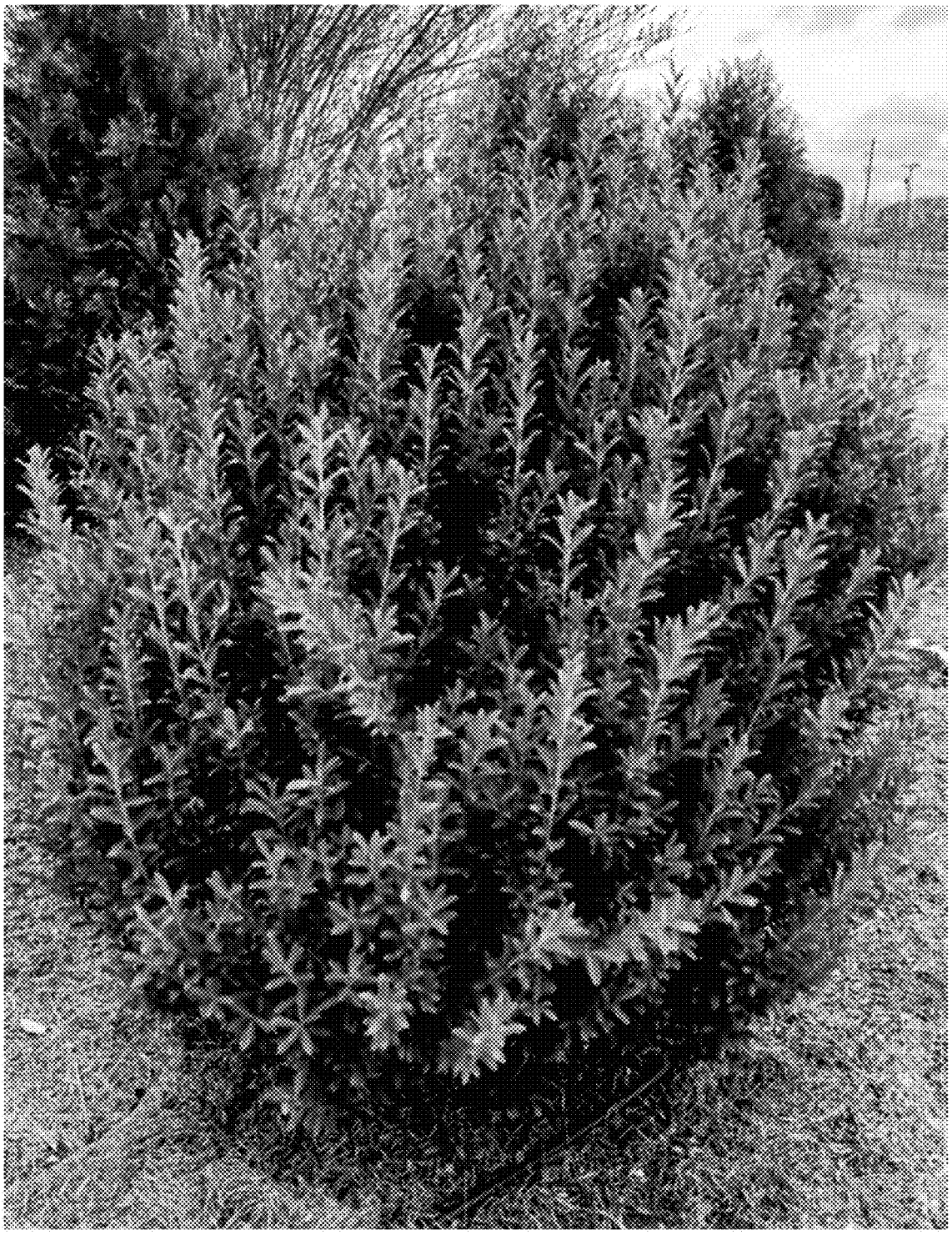
FIG. 1 is a photograph of a three-year-old 'RutHol10' plant (four years from cutting) and depicts the overall globose plant habit of 'RutHol10'.
Figure 2:
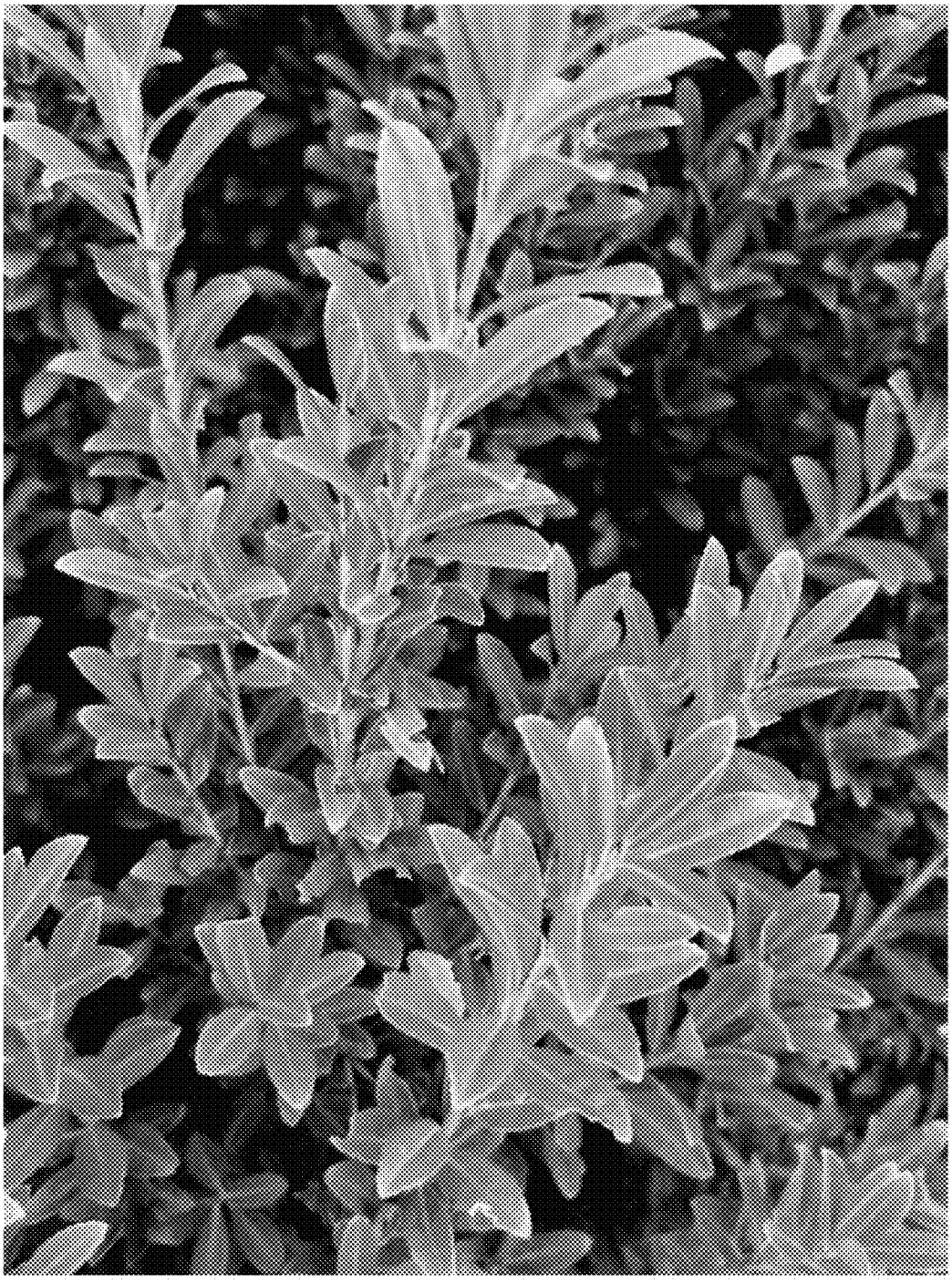
FIG. 2 depicts a close-up view of foliage of the 'RutHol10' plant of FIG. 1.

The following traits have been consistently observed in the original plants of the new 'RutHol10' and in asexually propagated progeny grown in Watkinsville, Georgia, and, to the best knowledge of the inventors, their combination forms the unique characteristics of the new variety *Ilex* 'RutHol10'. The following is a detailed description of the *Ilex* x cultivar named 'RutHol10'. Data was collected from plants growing in a horticultural farm at Watkinsville, GA; specifically, from four-year-old plants grown outdoors in containers. The average temperatures ranged from extreme lows of about 20° F. to 30° F. in the winter, and extreme highs of about 90° F. to 100° F. in summer.

Throughout this specification, color names beginning with a small letter signify that the name of that color, as used in common speech, is aptly descriptive. Color names beginning with a capital letter designate values based upon The R.H.S. Colour Chart, 3$^{rd}$ edition published in 1995 by The Royal Horticultural Society (R.H.S.), London, England.

Parentage: Female parent—*Ilex crenata* 'Sky Pencil' x *Ilex maximowicziana* (female, F1); Male parent—*Ilex crenata* x *Ilex maximowicziana* (male, F1).

Growth and propagation: Propagation type—vegetative terminal cuttings; growth rate—moderate; root description—typically about 4-8 roots arising from the base of the cuttings; rooting habit—moderate.

Plant description:

Habit: Upright, oval shrub.

Usage: Various uses, including landscaping, ornamental, container, border, hedge, and mass planting.

Vigor: Moderate to vigorous.

Size of plant: Three-gallon size container plant, four years from cutting.

A. *Height*.—From soil level to top of plant, about 48 in.
B. *Width*.—About 48 in.

Stem:

A. *Color* (*R.H.S.*).—Yellow-Green 144A.
B. *Strength*.—Moderate.
C. *Length*.—About 10-30 cm.
D. *Diameter*.—About 2-3 mm.
E. *Texture/pubescence*.—Moderately hispid.
F. *Shape*.—Ridged, 5-sided.
G. *Odor* (*of bruised stem*).—None.
H. *Internode length*.—About 4-6 mm.
I. *Shoot angle*.—About 65 degrees.
J. *Quantity*.—Numerous, with an average of about 6 main branches and about 3 lateral branches per main branch.
K. *Lenticles*.—Absent.

Leaf:

A. *Type*.—Simple.
B. *Color* (*R.H.S.*).—1. Upper leaf surface: mature growth — Yellow-Green 146A, new growth — Green 137B. 2. Lower leaf surface: emerging and mature — Yellow-Green 146B.
C. *Mature size* (*l*×*w*).—About 3.5cm×1 cm.
D. *Apex*.—Acute.
E. *Base*.—Attenuate.
F. *Margin*.—Serrulate.
G. *Shape*.—Lanceolate.
H. *Lobes* (*present/absent*).—Absent.
I. *Pubescence*.—Absent.
J. *Arrangement on stem*.—Alternate.
K. *Venation*.—Pinnate, Yellow Green 153A.
L. *Texture*.—Leathery (both upper and lower surfaces).
M. *Odor when crushed*.—None.
N. *Leaf number*.—Average of about 2 per cm/stem.

Petiole:

A. *Length*.—About 4-5 mm.
B. *Shape*.—Oval.
C. *Color* (*R.H.S.*).—Yellow-Green 146B.
D. *Texture/pubescence*.—Moderately hispid.
E. *Diameter*.—About 1 mm.

Inflorescence:

A. *Type*.—Solitary to flowered Cyme.
B. *Number per plant*.—Numerous.
C. *Longevity*.—About three weeks.

Flower:

A. *Type*.—Male, dioecious.
B. *Number per inflorescence*.—3-5 per inflorescence; Numerous inflorescences per plant.
C. *Axillary or terminal*.—Axillary.
D. *Symmetry*.—Regular.
E. *Size* (*l*×*w*).—About 1 mm×1 mm.
F. *Fragrance*.—None.
G. *Bud*.—1. Size (l×w): about 1 mm×1 mm. 2. Shape: Ovate. 3. Color (R.H.S.): Yellow-Green 144A. 4. Pubescence: Smooth, no pubescence.
H. *Blooms*.—1. First bloom: late April. 2. Peak bloom: early May. 3. Longevity: about 3-5 days.
I. *Petals*.—1. Number: about 4. 2. Size (l×w): about 1 mm×1 mm. 3. Shape: Ovate. 4. Apex: Round. 5. Base: Truncate. 6. Margin: Smooth, entire. 7. Color at Peak Bloom: (R.H.S.) Yellow-Green 145C. 8. Texture/Pubescence: Smooth, no pubescence. 9. Arrangement: Symmetrical.

J. *Pedicels.*—1. Color (R.H.S.): Yellow-Green 144A. 2. Texture/Pubescence: slight. 3. Length: about 3-4 mm. 4. Aspect: Erect. 5. Strength: Strong.

K. *Sepals.*—1. Number: about 4. 2. Size (l×w): about 1 mm×1 mm. 3. Shape: acuminate. 4. Texture/Pubescence: None. 5. Color (R.H.S.): Yellow Green 144A. 6. Apex acute. 7. Base rounded.

L. *Stamens.*—1. Number: about 4. 2. Anther: a) Size (l×w): about 0.5 mm×0.5 mm. b) Shape: Oval. c) Color (R.H.S.): Yellow 11B. d) Texture/Pubescence: no pubescence. 3. Filament: a) Size (l×w): about 1 mm×0.5 mm. b) Color (R.H.S.): Green-White 157D. c) Texture/Pubescence: Smooth, no pubescence. 4. Pollen: a) Quantity: Moderate. b) Color (R.H.S.): Yellow 11B.

L. *Pistils.*—1. Description: visible but reduced in size since this cultivar is a male plant. 2. Ovary size (l×w) — about 1 mm×1 mm, color —Yellow-Green 150D, texture — minutely 4 lobed, pubescence — none. 3. Stigma shape — oblong; color (R.H.S.) — Yellow Green 146B, Texture — smooth; pubescence — none. 4. Style — size (l×w) — about 2mm×1 mm; White 155B; texture — smooth, pubescence — none.

Fruit & seed: Since 'RutHol10' is a male cultivar, no fruit and seed is produced.

Pest and disease resistance: To date, plants of the new *Ilex* have been observed to have resistance to spider mites, *Tetranychus urticae.*

Hardiness: Not fully determined. To date, the plants have been grown in USDA Zone 8a in Watkinsville, GA, experiencing 6° F. in December 2022 with no damage. Parental species have survived −5° F. with no damage in Blairsville, GA (USDA zone 6b).

What is claimed is:

1. A new and distinct cultivar of the *Ilex* plant named 'RutHol10' as illustrated and described herein.

* * * * *